(12) United States Patent
Miller et al.

(10) Patent No.: US 6,804,543 B2
(45) Date of Patent: Oct. 12, 2004

(54) SENSOR FOR TRANSCUTANEOUS MEASUREMENT OF VASCULAR ACCESS BLOOD FLOW

(75) Inventors: David R. Miller, Morgan, UT (US); David A. Bell, Farmington, UT (US); Douglas L. Cox, Morgan, UT (US); Songbiao Zhang, Sandy, UT (US)

(73) Assignee: Hema Metrics, Inc., Kaysville, UT (US)

( * ) Notice: Subject to any disclaimer, the term of this patent is extended or adjusted under 35 U.S.C. 154(b) by 0 days.

(21) Appl. No.: 10/099,974

(22) Filed: Mar. 19, 2002

(65) Prior Publication Data

US 2002/0133066 A1 Sep. 19, 2002

Related U.S. Application Data

(63) Continuation-in-part of application No. 09/750,076, filed on Dec. 29, 2000, now Pat. No. 6,725,072.

(51) Int. Cl.$^7$ ................................................ A61B 5/00
(52) U.S. Cl. ...................................... 600/310; 600/322
(58) Field of Search ................................ 600/310, 316, 600/322–329, 333–344, 504

(56) References Cited

U.S. PATENT DOCUMENTS

| | | |
|---|---|---|
| 3,638,640 A | 2/1972 | Shaw |
| 3,880,151 A | 4/1975 | Nilsson et al. |
| 4,014,321 A | 3/1977 | March |
| 4,081,372 A | 3/1978 | Atkin et al. |
| 4,086,915 A | 5/1978 | Kofsky et al. |
| 4,167,331 A | 9/1979 | Nielsen |
| 4,181,610 A | 1/1980 | Shintani et al. |
| 4,223,680 A | 9/1980 | Jöbsis |
| 4,266,554 A | 5/1981 | Hamaguri |
| 4,295,470 A | 10/1981 | Shaw et al. |
| 4,416,285 A | 11/1983 | Shaw et al. |
| 4,446,871 A | 5/1984 | Imura |
| 4,653,498 A | 3/1987 | New, Jr. et al. |
| 4,655,225 A | 4/1987 | Dahne et al. |

(List continued on next page.)

FOREIGN PATENT DOCUMENTS

| | | |
|---|---|---|
| EP | 104772 B1 | 4/1984 |
| EP | 160768 B1 | 11/1985 |
| EP | 0 529 412 | 3/1993 |
| EP | 0 928 614 | 7/1999 |
| WO | WO 86/06946 | 12/1986 |
| WO | WO 89/01758 | 3/1989 |
| WO | WO 93/06456 | 4/1993 |

OTHER PUBLICATIONS

W. Cui, "Photon Diffusion Theory and Noninvasive Tissue Optical Property Measurement," PhD. Thesis, Biomedical Engineering Department, Rensselaer Polytechnic Institute (1990).

J.P. Payne and J.W. Severinghaus, Eds., *Pulse Oximetry*, Chapters 1 and 2 (©1986).

John D. Bower and Thomas G. Coleman, "Circulatory Function During Chronic Hemodialysis," vol. XV *Trans. Amer. Soc. Artif. Int. Organs*, 1969, 373–377.

(List continued on next page.)

*Primary Examiner*—Eric F. Winakur
*Assistant Examiner*—David J. McCrosky
(74) *Attorney, Agent, or Firm*—Jacobson Holman PLLC

(57) ABSTRACT

An optical sensor includes a sensing pair of complementary emitter and detector elements for measuring the bulk absorptivity ($\alpha$) of an area parallel to and including a hemodialysis access site, and a normalizing pair of complementary emitter and detector elements for measuring the absorptivity ($\alpha_o$) of the tissue itself perpendicular to the access site. The pairs of emitter and detector elements define two lines at right angles to each other, and one of the pairs lies to one side of the line defined by the other of the pairs, such that the two pairs of emitter and detector elements form a "T" shape. Indicator dilution techniques are used to measure vascular access flow rates during routine hemodialysis, using the sensor.

17 Claims, 7 Drawing Sheets

U.S. PATENT DOCUMENTS

| | | | |
|---|---|---|---|
| 4,685,464 A | 8/1987 | Goldberger et al. | |
| 4,714,080 A | 12/1987 | Edgar, Jr. et al. | |
| 4,770,179 A | 9/1988 | New et al. | |
| 4,805,623 A | 2/1989 | Jöbsis | |
| 4,819,752 A | 4/1989 | Zelin | |
| 4,821,734 A | 4/1989 | Koshino | |
| 4,824,242 A | 4/1989 | Frick et al. | |
| 4,825,872 A | 5/1989 | Tan et al. | |
| 4,825,879 A | 5/1989 | Tan et al. | |
| 4,832,484 A | 5/1989 | Aoyagi et al. | |
| 4,863,265 A | 9/1989 | Flower et al. | |
| 4,867,557 A | 9/1989 | Takatani et al. | |
| 4,920,972 A | 5/1990 | Frank et al. | |
| 4,925,299 A | 5/1990 | Meisberger et al. | |
| 5,028,787 A | 7/1991 | Rosenthal et al. | |
| 5,035,243 A | 7/1991 | Muz | |
| 5,048,524 A | 9/1991 | Bailey | |
| 5,054,487 A | 10/1991 | Clarke | |
| 5,057,695 A | 10/1991 | Hirao et al. | |
| 5,058,587 A | 10/1991 | Kohno et al. | |
| 5,059,394 A | 10/1991 | Phillips et al. | |
| 5,066,859 A | 11/1991 | Karkar et al. | |
| 5,092,836 A | 3/1992 | Polaschegg | |
| 5,099,841 A | 3/1992 | Heinonen et al. | |
| 5,101,825 A | 4/1992 | Gravenstein et al. | |
| 5,111,817 A | 5/1992 | Clark et al. | |
| 5,127,406 A | 7/1992 | Yamaguchi | |
| 5,137,023 A | 8/1992 | Mendelson et al. | |
| 5,158,091 A | 10/1992 | Butterfield et al. | |
| H1114 H | 12/1992 | Schweitzer et al. | |
| 5,193,543 A | 3/1993 | Yelderman | |
| 5,237,999 A | 8/1993 | Von Berg | |
| 5,285,783 A | 2/1994 | Secker | |
| 5,351,686 A | 10/1994 | Steuer et al. | |
| 5,372,136 A | 12/1994 | Steuer et al. | |
| 5,456,253 A | 10/1995 | Steuer et al. | |
| 5,499,627 A | 3/1996 | Steuer et al. | |
| 5,520,177 A | 5/1996 | Ogawa | |
| 5,551,422 A | 9/1996 | Simonsen et al. | |
| 5,595,182 A | 1/1997 | Krivitski | |
| 5,692,503 A | 12/1997 | Kuenstner | |
| 5,785,657 A | 7/1998 | Breyer et al. | |
| 5,797,841 A | 8/1998 | Delonzor et al. | |
| 5,803,908 A | 9/1998 | Steuer et al. | |
| 5,817,009 A | 10/1998 | Rosenheimer et al. | |
| 5,830,132 A | 11/1998 | Robinson | |
| 5,857,462 A | 1/1999 | Thomas et al. | |
| 5,924,979 A | 7/1999 | Swedlow et al. | |
| 5,974,337 A | * 10/1999 | Kaffka et al. | 600/316 |
| 6,117,099 A | 9/2000 | Steuer et al. | |
| 6,167,765 B1 | 1/2001 | Weitzel | |
| 6,181,958 B1 | 1/2001 | Steuer et al. | |
| 6,189,388 B1 | 2/2001 | Cole et al. | |
| 6,210,591 B1 | 4/2001 | Krivitski | |
| 6,246,894 B1 | 6/2001 | Steuer et al. | |
| 6,452,371 B1 | 9/2002 | Brugger | |

OTHER PUBLICATIONS

Larry Reynolds, C. Johnson, A. Ishimaru, "Diffuse reflectance from a finite blood medium: applications to the modeling of fiber optic catheters," Sep. 1976, vol. 15, No. 9, *Applied Optics*, pp. 2059–2067.

R.N. Greenwood, C, Aldridge, L. Goldstein, L.R.I. Baker and W.R. Cattell, "Assessment of arteriovenous fistulae from pressure and thermal dilution studies: clinical experience in forearm fistulae," *Clinical Nephrology*, vol. 23, NO. 4–1985, pp. 189–197.

R.N. Greenwood, C. Aldridge and W.R. Cattell, "Serial blood water estimations and in–line blood viscometry: the continuous measurement of blood volume during dialysis procedures," *Clinical Science* (1984)66, pp. 575–583.

C. Aldridge, R.N. Greenwood, W.R. Cattell and R.V. Barrett, "The assessment of arteriovenous fistulae created for haemodialysis from pressure and thermal dilution measurements," *Journal of Medical Engineering & Technology*, vol. 8, No. 3, (May/Jun.), pp. 118–124.

L. Goldstein, L. Pavitt, R.N. Greenwood, C. Aldridge, L.R.I. Baker and W.R. Cattell, "The Assessment of Areteriovenous Fistulae From Pressure and Recirculation Studies," *ProcEDTNA–ERCA* (1985) vol. 14, pp. 207–215.

R.N. Greenwood, C. Aldridge, L. Goldstein, L.R.I. Baker and W.R. Cattell, "Assessment of Arteriovenous Fistulas From Pressure and Recirculation Studies: Clinical Experience In 215 Upper Limb Fistulas," *ProcEDTA–ERA* (1985), vol. 22, pp. 296–302.

Joseph M. Schmitt, James D. Meindl and Frederick G. Mihm, "An Integrated Circuit–Based Optical Sensor for In Vivo Measurement of Blood Oxygenation," *IEEE Transactions On Biomedical Engineering*, vol. BME–33, No. 21, Feb. 1986, pp. 98–107.

Joseph M. Schmitt, Fred G. Mihm and James Meindl, *New Methods for Whole Blood Oximetry*, Annals of Biomedical Engineering, vol., 14, pp. 35–52, 1986.

Mark R. Arnfield, J. Tulip and Malcolm McPhee, "Optical Propagation in Tissue With Anisotropic Scattering," *IEEE Transactions on Biomedical Engineering*, vol. 35, No. 5, May 1988, pp. 372–381.

N.M. Krivitski, "Theory and validation of access flow measurements by dilution technique during hemodialysis," *Kidney Int* 48:244–250, 1995.

N.M. Krivitski, "Novel method to measure access flow during hemodialysis by ultrasound velocity dilution technique," *ASAIO J* 41:M741–M745, 1995.

T.A. Depner and N.M. Krivitski, "Clinical measurement of blood flow in hemodialysis access fistulae and grafts by ultrasound dilution," *ASAIO J* 41:M745–M749, 1995).

D. Yarar et al., "Ultrafiltration method for measuring vascular access flow rates during hemodialysis," *Kidney Int.*, 56: 1129–1135 (1999).

N.M. Krivitski et al., "Saline Release Method to Measure Access Flow (AF) by Ultrasound Dilution during Hemodialysis," *JASN Abstracts*, 8:164A, 1997.

W. Cui et al., "Experimental Study of Migration Depth for the Photons Measured at Sample Surface," SPIE, vol. 1431, pp 180–191 (1991).

S. Feng et al., "Monte Carlo Simulations of Photon Migration Path Distributions in Multiple Scattering Media," SPIE, vol. 1888, pp 78–89 (1993).

* cited by examiner

SENSOR FOR TRANSCUTANEOUS MEASUREMENT OF VASCULAR ACCESS BLOOD FLOW

CROSS REFERENCE TO RELATED APPLICATION(S)

This application is a continuation-in-part of application Ser. No. 09/750,076, filed Dec. 29, 2000; (now U.S. Pat. No. 6,725,072), which is incorporated herein by reference in its entirety.

FIELD OF THE INVENTION

The present invention relates to apparatus for non-invasively measuring one or more blood parameters. More specifically, the invention relates to apparatus for the transcutaneous measurement of vascular access blood flow ("TQA") that is capable of generating accurate TQA measurements, even when the volume of access being measured is extremely small in size or extremely deep or when the access is of varying nature, such as a synthetic or native fistula. Further, it is possible to infer additional information about the access area, such as collateral veins or competing vessels.

BACKGROUND OF THE INVENTION

Access blood flow for hemodialysis patients can now be measured non-invasively through a novel photo-optic transcutaneous technique as described in co-pending application Ser. No. 09/750,122, filed Dec. 29, 2000 (which is incorporated herein by reference in its entirety), using a transcutaneous TQA sensor as disclosed in application Ser. No. 09/750,076, filed Dec. 29, 2000 (which is also incorporated herein by reference in its entirety), and more particularly, the transcutaneous TQA sensor described in connection with FIGS. 2–6 thereof (hereinafter, "the prior art linear sensor").

With reference to FIGS. 1, 2, and 2A, the prior art linear sensor 10 includes two light emitting sources (emitters) 12$a$ and 12$b$, preferably light emitting diodes (LEDs) of specific wavelengths, and two complementary silicon photodiode detectors 14$a$ and 14$b$ alternatingly arranged in a straight line at identical intervals to form three LED/detector pairs with identical separations between the members of each pair, for the purpose of measuring the bulk absorptivity ($\alpha$) of the volume immediately surrounding and including the access site A, and the absorptivity ($\alpha_o$) of the tissue itself. The LEDs preferably emit light at a wavelength of 805 nm–880 nm, because it is near the known isobestic wavelength for hemoglobin, is commercially available, and has been shown to be effective in the optical determination of whole blood parameters such as hematocrit and oxygen saturation.

The technique is accomplished by directly placing the prior art linear sensor 10 on the skin of a patient with the aligned emitters 12$a$ and 12$b$ and detectors 14$a$ and 14$b$ perpendicular to the vascular access site A, and measuring the back-scattered light from a turbid tissue sample to determine the percentage change in hematocrit $\Delta H$ as a bolus of saline passes through the access vessel.

When the prior art linear sensor 10 is placed on the surface of the skin, each LED 12$a$ and 12$b$ illuminates a volume of tissue T, and a small fraction of the light absorbed and back-scattered by the tissue and red blood cells is detected by its adjacent photodetector 14$a$ or 14$b$, which generates a detection signal. When the volume of tissue illuminated includes all or even part of the access A, the resultant $\alpha$ value includes information about both the surrounding tissue T and the access itself. In order to resolve the signal due to blood flowing within the access A from that due to the surrounding tissues T, the prior art linear sensor 10 illuminates adjacent tissue regions T on either side of the access A. Values of $\alpha_o$ for tissue regions T not containing the access A are then used to normalize the signal, thus providing a baseline from which relative changes can be assessed in access hematocrit in the access blood flowing directly under the skin. The intensity of the signal produced by each photodetector 14A or 14B is proportional to the total absorption and scattering within a given volume of tissue between each detector 14$a$ or 14B and its adjacent LED 12$a$ or 12$b$. During saline dilution, only the hematocrit inside the access A varies, and the detected signal changes are solely dependent upon the optical property changes within the small volume of access viewed by the sensor 10.

By correcting the signal in the volume containing the access A with the average reference signal in the volumes without access, the sensor 10 provides a signal solely dependent on the hematocrit flowing in the access. Then, traditional Ficke principle mathematics can be used to calculate the blood flow rate using the following equation:

$$Q_a = \frac{V}{\int \frac{\Delta H(t)}{H_a} dt}$$

For a given separation between LED and photodiode in the sensor 10, the volume of tissue illuminated and viewed by the prior art linear sensor 10 is relatively constant and the signal-to-noise ratio of this technique depends on the volume of access included inside the tissue volume. When the volume of access included inside the tissue volume is small enough due to extremely small size or excessive depth, the signal-to-noise ratio falls to a level that would not generate accurate measurement results. It would accordingly be desirable to improve the signal-to-noise ratio so that accurate measurements can be taken even when the access is extremely small or very deep.

According to W. Cui ("Photon Diffusion Theory and Noninvasive Tissue Optical Property Measurement," PhD. Thesis, Biomedical Engineering Department, Rensselaer Polytechnic Institute (1990)), the principle path of diffused photons in a turbid medium is in the gradient direction of the photon density distribution, which is perpendicular to the contour surfaces. Along this direction, photons consistently travel all the way from the LED to the detector in a curved path. In a later study, W. Cui et al. ("Experimental Study of Migration Depth for the Photons Measured at Sample Surface," SPIE, Vol. 1431, pp 180–191 (1991)) further showed that the photon flux path from LED to detector has a "banana" shape that reaches deepest into the tissue at the mid-portion of the "banana." More significantly, in this "banana"-shaped photon path, there is a region in the middle between LED and detector near the tissue surface that is totally outside the detected photon flux path. This means that anything in this region will not interact with the photons that reach the detector and will never be "seen" by the detector. This finding was verified by S. Feng et al. ("Monte Carlo Simulations of Photon Migration Path Distributions in Multiple Scattering Media," SPIE, Vol. 1888, pp 78–89 (1993)), using both analytical perturbative diffusion theory and Monte Carlo simulations. This phenomenon also explains the clinical observations that with a visually observable shallow graft, no significant difference in $\alpha$ is detected with the injection of a saline bolus.

The configuration of the prior art linear sensor 10 allows it (or more precisely, the aligned LEDs 12a and 12b and the detectors 14 a and 14b) to be perpendicular to the access A and the photon flux F to travel across the access to generate an illuminated volume of access within the illuminated tissue volume, as shown in FIGS. 1 and 2. For a graft in the center of the photon flux path F, the volume of the access viewed by the prior art linear sensor 10 is limited to the cross-section of the graft and the photon flux path F as indicated by FIGS. 1 and 2. For a graft that is nearly out of the photon flux path F (because it is too shallow, as shown in FIG. 2A, or too deep) the volume of access "seen" by the prior art linear sensor 10 is so small that the signal-to-noise ratio is too low to give accurate measurements.

It is to the solution of this and other problems that the present invention is directed.

BRIEF SUMMARY OF THE INVENTION

It is therefore a primary object of the present invention to provide apparatus for non-invasively measuring one or more blood parameters associated with a vascular access, even when the volume of access being measured is extremely small in size or extremely deep.

It is another object of the present invention to provide a sensor for transcutaneous TQA measurement that is capable of generating accurate TQA measurements, even when the volume of access being measured is extremely small in size or extremely deep.

This and other objects of the invention is achieved by the provision of an optical sensor including two pairs of complementary emitter and detector elements, wherein the pairs of emitter and detector elements define two lines at right angles to each other, for the purpose of measuring the bulk absorptivity ($\alpha$) of the volume immediately surrounding and including the access site, and the absorptivity ($\alpha_o$) of the tissue itself.

In one aspect of the invention, one of the pairs lies to one side of the line defined by the other of the pairs, such that the two pairs of emitter and detector elements form a "T" shape.

In another aspect of the invention, each pair of emitter and detector elements comprises an LED of specific wavelength and a complementary photodetector. A wavelength of 805 nm–880 nm, which is near the known isobestic wavelength for hemoglobin, is used.

DETAILED DESCRIPTION OF THE INVENTION

Figure 1:
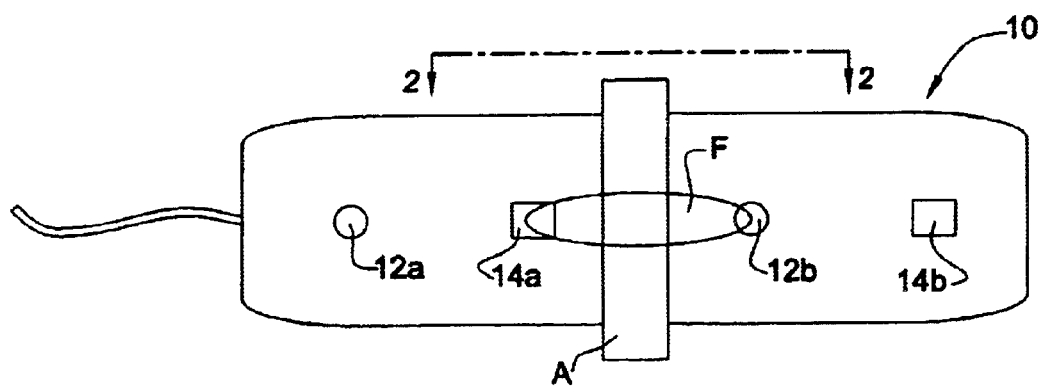
FIG. 1 is a bottom diagrammatic view of a prior art TQA sensor in place over a vascular access site.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

Referring now to FIGS. 3–7, there is shown a sensor 100 for the transcutaneous measurement of vascular access blood flow in a hemodialysis shunt or fistula A in accordance with the present invention. The sensor 100 comprises a body 102 having upper and lower surfaces 102a and 102b, a surrounding exterior cover 104, a first emitter/detector element pair 106a–106b set into the exterior cover 104 on the lower surface of the body 102, and a second emitter/detector element pair 108a–108b set into the exterior cover 104 on the lower surface of the body 102. Preferably, the emitter elements 106a and 108a are LEDs of specific wavelengths, preferably, a wavelength of 805 nm–880 nm; and preferably, the detector elements 106b and 108b are silicon photodiode detectors that are complementary to the LEDs.

The pairs of emitter and detector elements 106a–106b and 108a–108b define two lines L1 and L2 at right angles to each other. One of the pairs lies to one side of the line defined by the other of the pairs, such that the lines L1 and L2 defined by the two emitter/detector element pairs 106a–106b and 108a–108b form a "T" shape. The emitter/detector element pair 106a–106b that defines the cross-bar of the "T" shape (the "sensing" emitter/detector element pair) is placed over and parallel to the access A and measures the bulk absorptivity $\alpha$ of the volume of the access site and the volume immediately below the access site. The emitter/detector element pair 108a–108b that defines the stem of the "T" shape (the "normalizing" emitter/detector element pair) thus is placed to one side of and perpendicular to the access A and measures the absorptivity $\alpha_o$ of a tissue region T that does not contain the access A.

It does not matter which element of the normalizing emitter/detector element pair 108a–108b is the element that is closer to the sensing emitter/detector element pair 106a–106b, as long as the geometry and spacing between the elements of the individual pairs are maintained. When the geometry and spacing between the elements of the individual pairs are maintained, the light path is symmetric and the placement of the emitter element and the detector element in each pair can be reversed with impunity.

Figure 2:
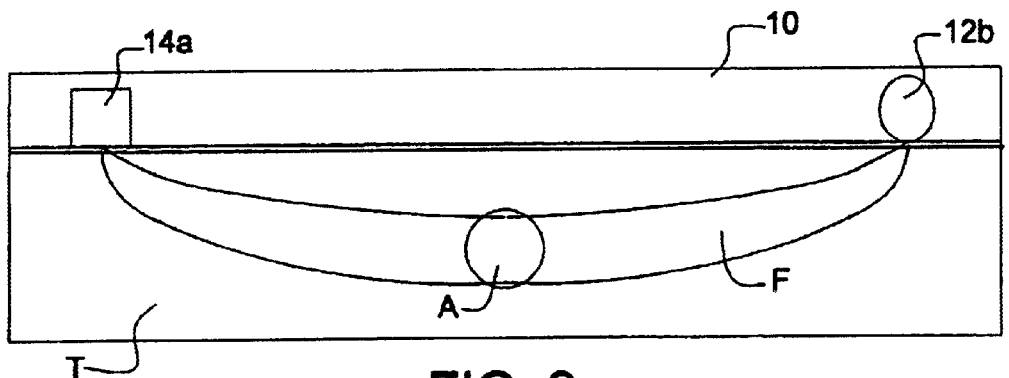
FIG. 2 is a cross-sectional view taken along line 2—2 of FIG. 1.
Figure 2A:
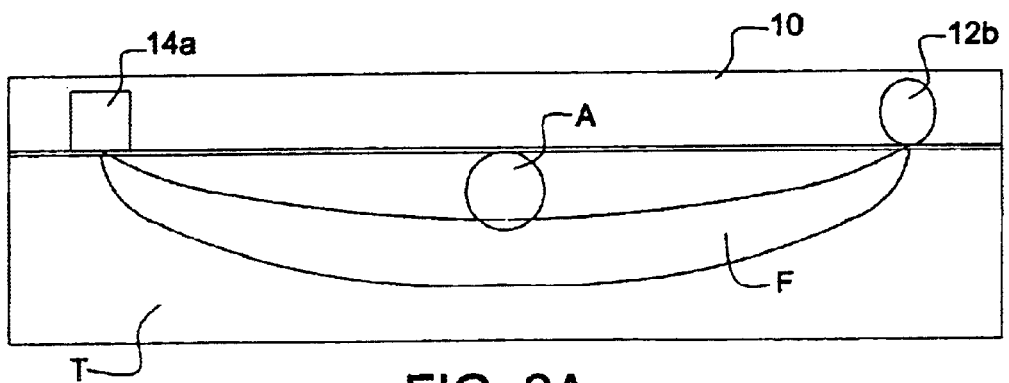
FIG. 2A is a cross-sectional view of a prior art TQA sensor in place over a very shallow vascular access site.
Figure 9:
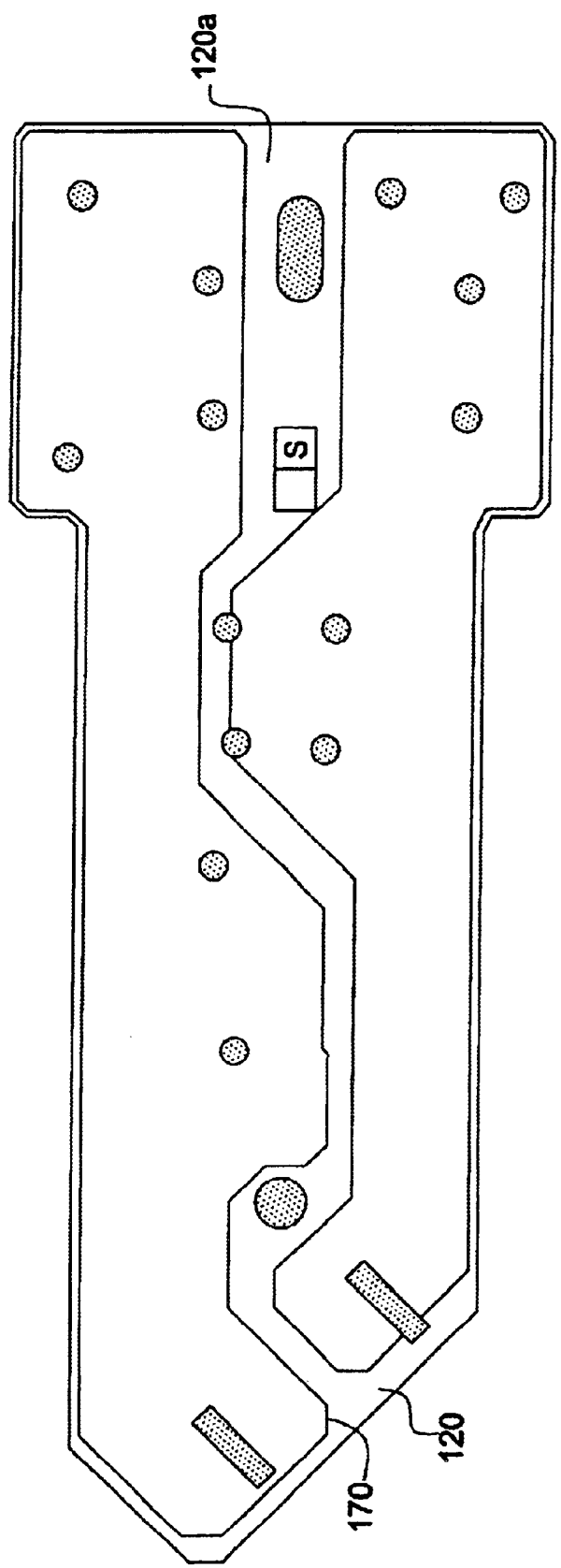
FIG. 9 is bottom plan view of the substrate of FIG. 8 and the circuitry thereon.
Figure 10:
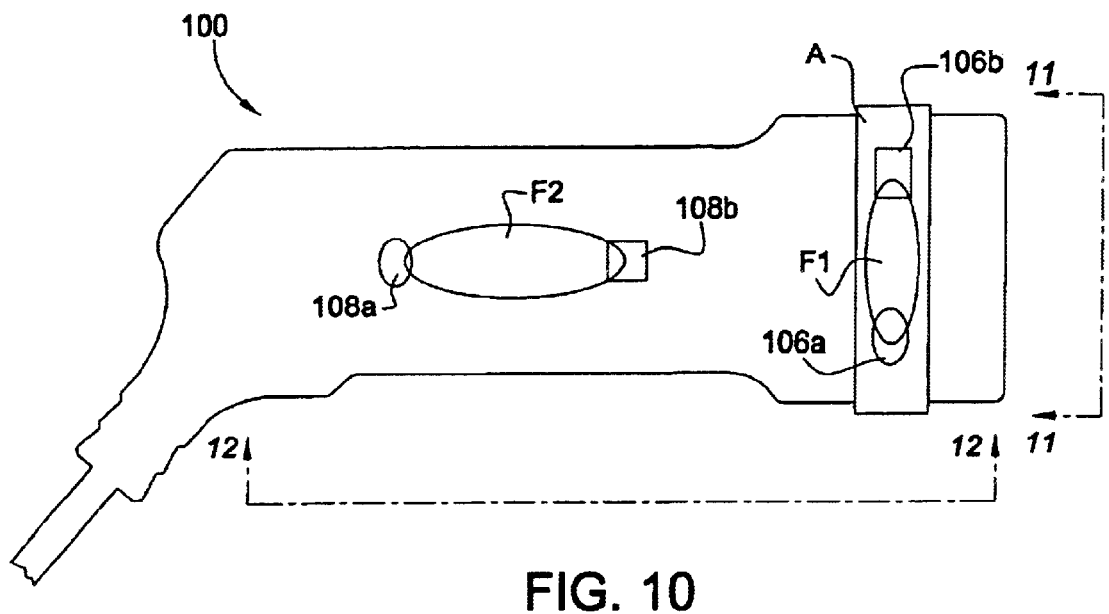
FIG. 10 is a bottom diagrammatic view of the TQA sensor of FIG. 3, in place over a vascular access site.
Figure 11:
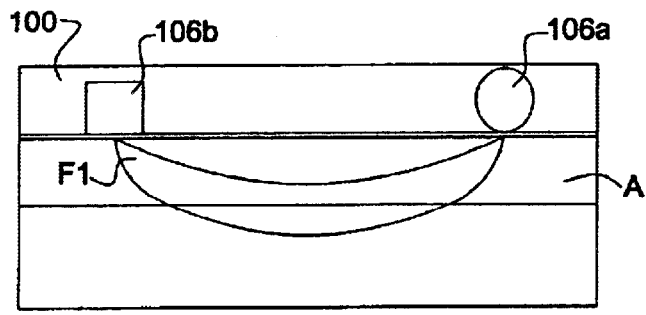
FIG. 11 is a cross-sectional view taken along line 11—11 of FIG. 10.
Figure 12:
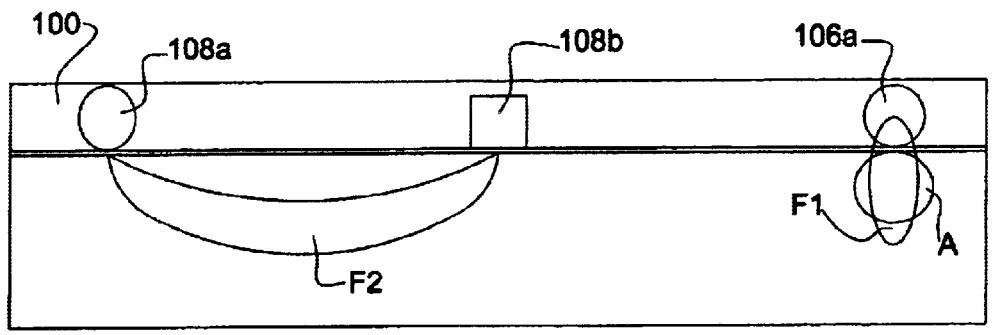
FIG. 12 is a cross-sectional view taken along line 12—12 of FIG. 10.
Figure 13:
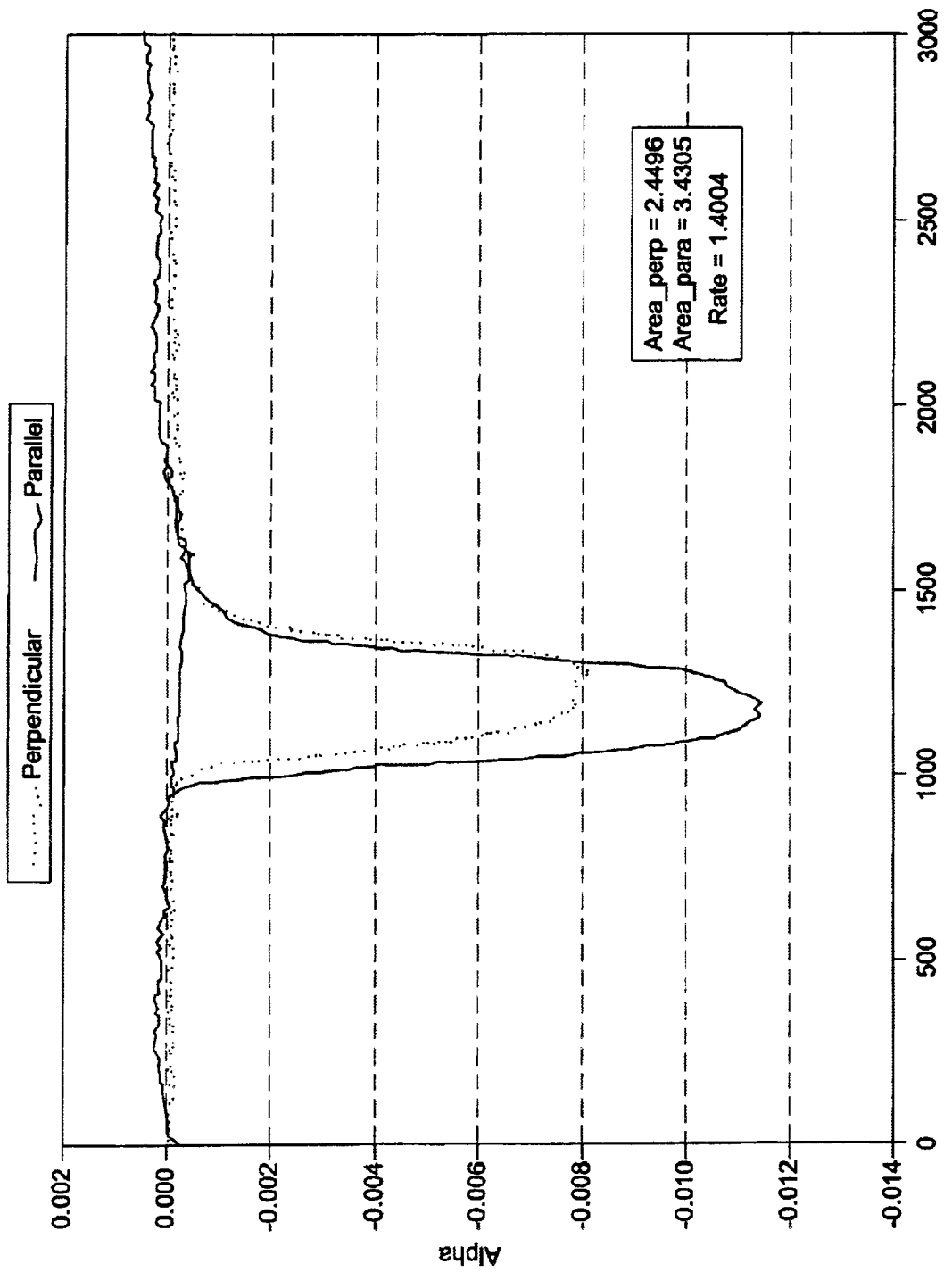
FIG. 13 is a graph comparing the signal change detected by the TQA sensor of FIG. 3 to the signal change detected by the prior art TQA sensor of FIG. 1.

With the "T" shape of the sensor 100, the sensing emitter/detector element pair 106a–106b is parallel to the access A and the photon flux path F is along the access line as shown in FIGS. 10–12. For a graft within a normal photon flux path, the volume of access viewed by the detector element 106b of the sensing emitter/detector element pair 106a–106b is larger than the volume viewed by the detectors 14a and 14b in the prior art linear sensor 10 of FIGS. 1, 2, and 2A. The sensor 100 hence increases the detection limit and sensitivity of the measurements, as shown in FIG. 13. For those grafts that are nearly undetectable with the prior art linear sensor 10 configuration of FIGS. 1, 2, and 2A, the advantage of the "T"-shaped sensor 100 in accordance with the present invention is more significant, because the volume of access viewed by the detector is much larger at both ends of the "banana" shaped photon flux path F, as shown in FIG. 9. This increase in volume of access viewed makes the "T"-shaped sensor 100 in accordance with the present invention less sensitive to the depth of the graft within its scope.

Figure 3:
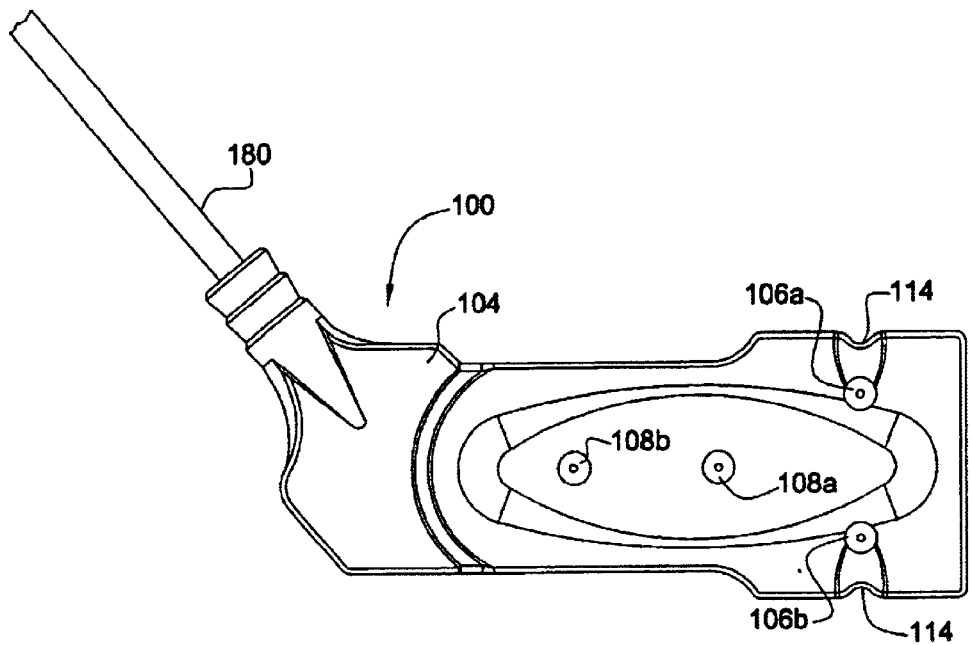
FIG. 3 is a bottom plan view of a TQA sensor in accordance with the present invention.
Figure 6:
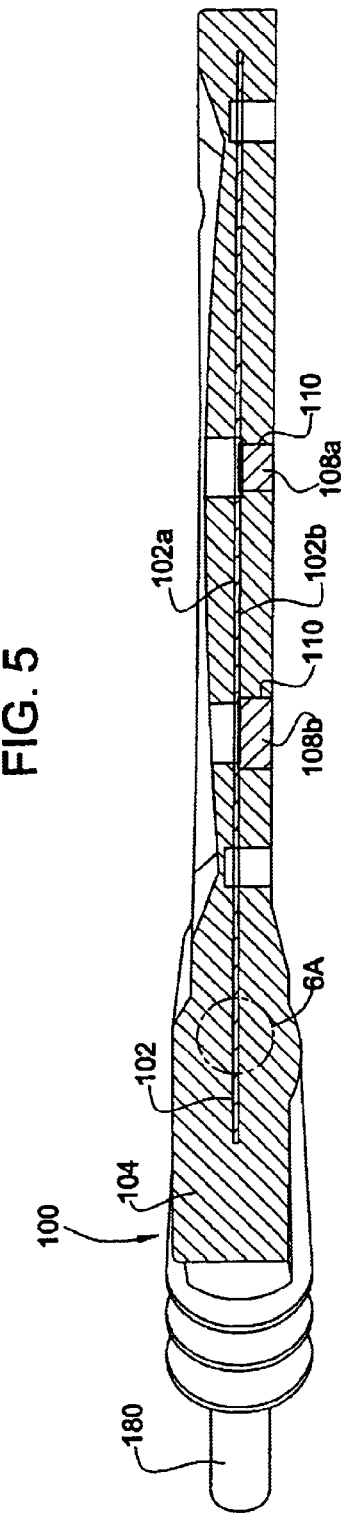
FIG. 6 is a cross-sectional view taken along line 6—6 of FIG. 3.
Figure 7:
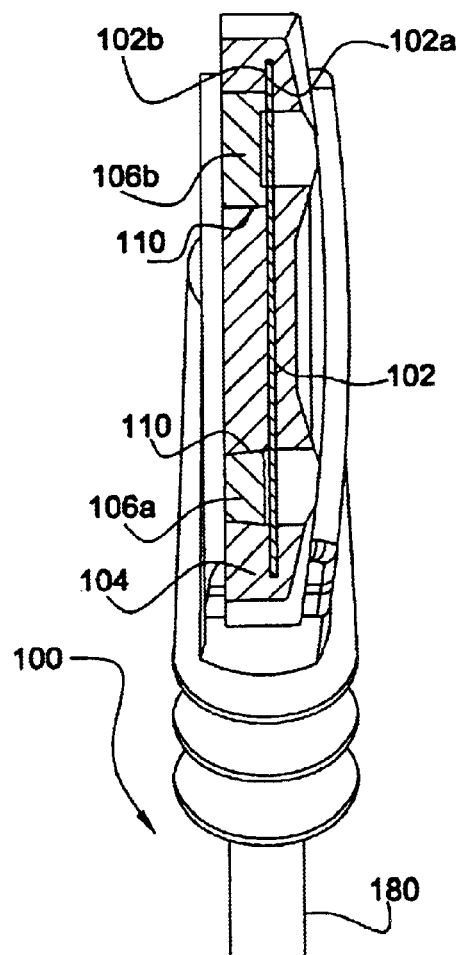
FIG. 7 is a cross-sectional view taken along line 7—7 of FIG. 3.
Figure 8:
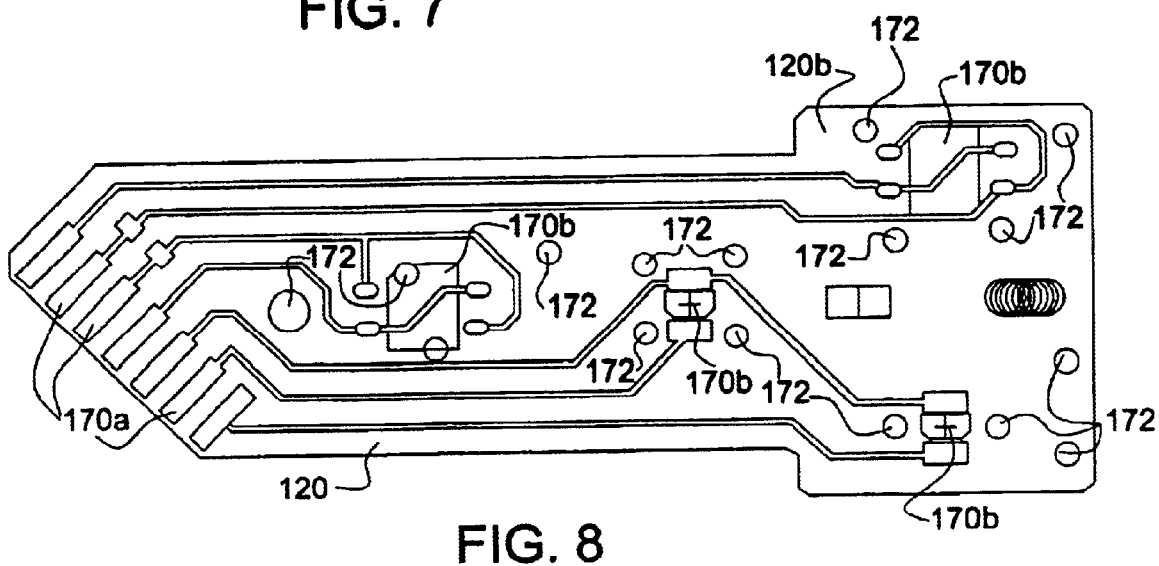
FIG. 8 is a top plan view of the substrate of the TQA sensor of FIG. 3.

As shown in FIGS. 3, 6, and 7, the exterior cover 104 is provided with apertures 110 in its lower surface (the surface that in use faces the access site) for receiving the emitters 106a and 108a and the detectors 106b and 108b. The apertures 110 are sized so that the emitters 106a and 108a and the detectors 106b and 108b lie flush with the lower surface of the body 102 (that is, the surface that contacts the skin). The upper surface of the exterior cover 104 may have a depression formed therein for manufacturing purposes. Alignment pins are used to hold the emitters 106a and 108a and detectors 106b and 108b on position during molding and leave the depressions after the sensor is removed from the mold.

Figure 4:
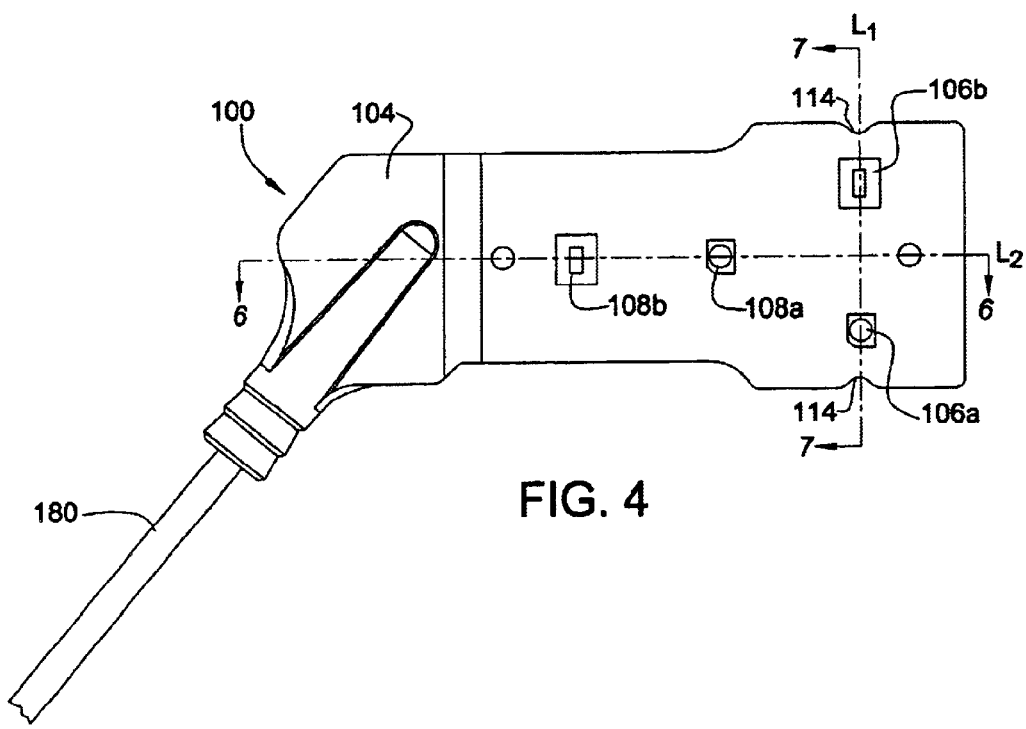
FIG. 4 is a top plan view of the TQA sensor of FIG. 3.
Figure 5:
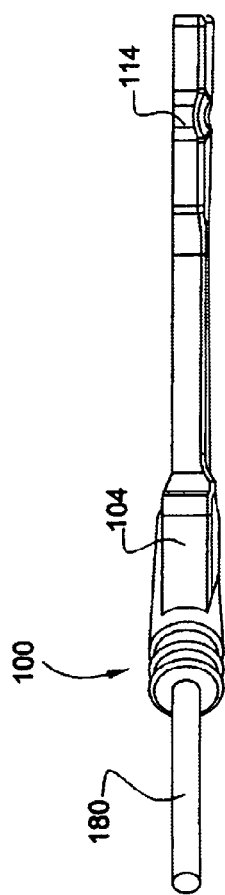
FIG. 5 is a side elevational view of the TQA sensor of FIG. 3.

Preferably, the exterior cover 104 is provided with markers 114 visible from the upper surface for guiding placement of the sensor 100 over the access. As shown in FIGS. 3–5, these markers 114 can take the form of indentations in the sides of the body 102. As will be appreciated by those of skill in the art, the markers 114 can also take other forms, such as printed or inscribed lines, arrows, or other markings.

Figure 6A:
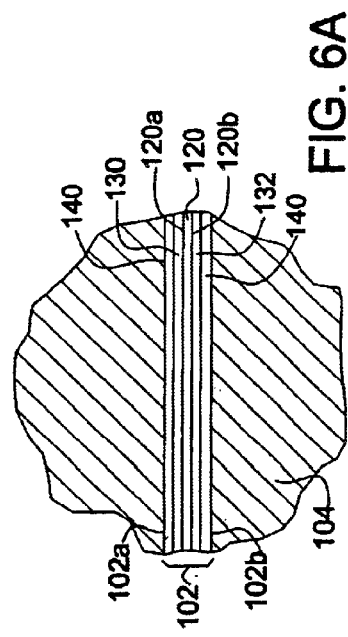
FIG. 6A is enlarged view of the area 6A of FIG. 6.

As shown in FIGS. 6 and 6A, the sensor body 102 is a laminate structure comprising a substrate 120 having upper and lower surfaces 120a and 120b, upper and lower conducting layers 130 and 132 overlying the upper and lower surfaces 120a and 120b, respectively, and defining the circuitry of the sensor 100, and a surrounding interior cover 140. As discussed in greater detail below, and as shown in FIG. 6A, there may also be outer upper and lower adhesive layers (not shown) between the upper and lower conducting layers and the interior cover 140 and inner upper and lower adhesive layers between the upper and lower surfaces 120a and 120b of the substrate 120 and the upper and lower conducting layers.

As shown in FIG. 9, the circuitry 170 associated with the emitter/detector element pairs 106a–106b and 108a–108b can be provided as a printed circuit on the upper and lower surfaces 120a and 120b of the substrate 120. The interior cover 140 over the upper conducting layer 130 has access holes therethrough (not shown) at the connector fingers 170a of the circuitry 170, and at the component pads 170b of the circuitry 170. Corresponding holes 172 are provided (e.g., by drilling) through the interior cover 140 to permit the emitter elements 106a and 108a and the detector elements 106b and 108b to be soldered to their respective component pads 170b.

The substrate 120 is made of a material, such as a polymide or polyimide-containing film, that is flexible enough to conform to the contours of the underlying tissue but rigid enough to have body durability. The exterior and interior covers 104 and 140 and the conducting layers 130 and 132 similarly must be flexible enough to conform to the contours of the underlying tissue but rigid enough to have body durability. For example, the interior cover 140 can be a flexible, dry-film, soldermask material, preferably a polyimide or other imide-containing film, which is applied over the substrate 120 and the conducting layers 130 and 132 in a tacky state with heat and vacuum and then oven cured onto the substrate 120 so that it bonds directly with the conductive layers 130 and 132. The purpose of a soldermask material being to encapsulate totally the underlying circuitry to protect it from the intended operating environment, the dry-film soldermask must be thick enough to flow over and around the component pads and traces of the circuitry during lamination. The substrate 120 and the upper and lower conducting layers 130 and 132 can be made of DuPont Pyralux® AP 9222 double-sided, copper-clad laminate, which is an all-polyimide composite of 2.0 mil polyimide film bonded to 2.8 mil 2 oz/ft² copper foil. The interior cover 140 can be made of 2.5 mil DuPont Pyralux® PC1025 photoimageable coverlay, which is a flexible, dry film solder mask consisting of a combination of acrylic, urethane, and imide-based material. The exterior cover 104 preferably is a plastic material such as urethane or silicone, and more particularly, a rubber silicon with, for example, a thickness of 1 mil. A rubber silicon material with a thickness of 1 mil has a durometer of 30.

The major consideration in the choice of the material and thickness of the substrate 120, the conducting layers 130 and 132, the interior cover 140, the adhesive (if any), and exterior cover 104 is the total flexibility of the sensor 100. That is, the net flexibility of the sensor 100 must meet the above stated requirements for rigidity. As will be appreciated by those of skill in the art, there are numerous combinations of materials and dimensions that will produce an acceptable flexibility.

The requirement for an outer upper and lower adhesive layer is dependent upon the composition of the interior cover 140, while the requirement for an inner upper and lower adhesive layer is dependent upon the composition of the substrate 120. For example, certain imide-containing films require an adhesive between the substrate 120 and the upper and lower conducting layers 130 and 132 because they do not incorporate any adhesive in their outer surfaces; while other imide-containing films incorporate a very thin layer of adhesive in their outer surfaces and are homogeneous after they are cured and thus do not require a separate adhesive layer between the substrate 120 and the upper and lower conducting layers 130 and 132. As each adhesive layer (when used) is about 1 mil thick, where it is desired to minimize the thickness of the sensor 100 (for example, to enable the sensor 100 to more easily conform to the surface of the skin where the access site sits near the surface of the skin, or on small arms where a the radius of curvature is tighter, or in general in any application requiring that the sensor 100 be more flexible) it is preferable to use materials for the substrate 120 and the interior cover 140 that do not require an adhesive.

The sensor 100 is connected to an associated monitoring system (not shown) by the cable 180. The monitoring system can be a computer including a computer processor and memory, and output means such as a video monitor and printer (not shown).

As shown in FIGS. 10–12, there are two "banana"-shaped photon flux paths in the tissue seen by the two detectors 106b and 108b: a first (or sensing) photon flux path F1 representing the reflective penetration volume ($\alpha$) of the sensing emitter element 106a through the access A and the access site tissue as seen by the sensing detector element 106b in the process of determination of the access Hematocrit H; and a second (or normalizing) photon flux path F2 representing the reflective penetration ($\alpha_o$) of the normalizing emitter element 108a through the non-access site tissue to one side of the access site as seen by the normalizing detector element 108b. The measurements of $\alpha$ and $\alpha_o$ can then be used to calculate $$F\left(\frac{\Delta H}{H}\right)$$

in accordance with Equation (13) of application Ser. No. 09/750,076.

In order to use indicator dilution techniques to measure vascular access flow rates during routine hemodialysis, the indicator must be injected upstream and its concentration detected downstream in the blood flowing through the vascular access site, as described in co-pending application Ser. No. 09/750,076. Because the sensor 100 can detect a dilution signal downstream of the venous needle through the skin, a unique application of indicator dilution principles permits determination of the vascular access flow rate without reversal of the dialysis blood lines. The sensor 100 can be used to carry out the various methods of measuring vascular access blood flow rate, as well as the method for locating accesses and grafts and localizing veins in normal patients, as described in co-pending application Ser. No. 09/750,122.

Due to the depth of the access site, in order for the full depth of the access site to be intersected by the first photon flux path F1, the spacing between the centers of the sensing emitter and detector elements 106a and 106b is typically about 16.8 mm. The spacing between the centers of the normalizing emitter and detector elements 108a and 108b also is typically about 16.8 mm. The spacing between the center of the normalizing detector 108b and the line L1 defined by the centers of the sensing emitter/detector element pair 106a–106b is typically about 16.6 mm. However, other separations can be used and may have advantages in controlling depths of penetration avoiding competing structures such as bone.

Also, an emitter element-detector element separation is required so that the reflectance of the first layer of tissue (a non-blood layer of epithelium) does not further exaggerate a multiple scattering effect, as discussed in U.S. Pat. No. 5,499,627, which is incorporated herein by reference in its entirety.

As indicated above, the emitter elements 106a and 106b are preferably LEDs that emit light at a wavelength of 805 nm–880 nm, and the detector elements 108a and 108b are silicon photodiodes, and the exterior cover 104 is formed by molding or other means such that the emitter elements 106a and 108a and the detector elements 106b and 108b lie flush with the lower surface of the exterior cover 104, that is, the surface that faces the skin, so that both of the emitter/detector element pairs 106a–106b and 108a–108b lie on the skin.

Finally, the sensor 100 can be fastened in place using surgical tape. Alternatively, the sensor can be made as a disposable adhesive patch that cannot be recalibrated and used again, as described in application Ser. No. 09/750,076.

All other factors remaining the same, when the emitter/detector element pairs 106a–106b and 108a–108b are arranged in a "T" shape in accordance with the present invention, rather than in a linear configuration as in the prior art linear sensor 10 of application Ser. No. 09/750,076, the volume of access, and thus the signal strength, are significantly improved. With the improvement in signal strength, the "T"-shaped sensor 100 in accordance with the present invention can detect some accesses that could not be identified by the prior art linear sensor 10; and the "T"-shaped sensor 100 in accordance with the present invention can accurately measure accesses that could not be viewed "clearly" by the prior art linear sensor 10. In effect, the "T"-shaped configuration of the sensor 100 in accordance with the present invention gives more accurate measurements to smaller, shallower, and/or deeper accesses.

As shown in FIG. 7, in vitro experimental results indicate that under the same experimental conditions, the signal change detected by the "T"-shaped sensor 100 in accordance with the present invention is about 40% higher than that detected by the prior art linear sensor 10. The increase in signal strength also increased the overall TQA calculation slope from 894 to 1187.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

We claim:

1. A sensor for the transcutaneous measurement of vascular access blood flow comprising:
    a body having upper and lower surfaces;
    sensing emitter/detector means on the lower surface of the body for positioning over and parallel to an access site for emitting and detecting light of a specific wavelength for measuring the bulk absorptivity $\alpha$ of the volume of the access site and the volume immediately below the access site; and
    normalizing emitter/detector means on the lower surface of the body for positioning to one side of and perpendicular to the access site for emitting and detecting light of the specific wavelength for measuring the absorptivity $\alpha_o$ of a tissue region that does not contain the access.

2. The sensor of claim 1, wherein the body comprises a substrate having upper and lower surfaces and circuitry associated with the emitter/detector element pairs provided on at least one of the surfaces of the substrate.

3. The sensor of claim 2, wherein the body further comprises an interior cover surrounding the substrate and the circuitry.

4. The sensor of claim 1, wherein the emitter elements are LEDs of specific wavelengths, and the detector elements are silicon photodiode detectors that are complementary to the LEDs.

5. The sensor of claim 4, wherein the LEDs have a wavelength of 805 nm–880 nm.

6. The sensor of claim 1, wherein one of the pairs lies to one side of the line defined by the other of the pairs, such that the two pairs of emitter and detector elements form a "T" shape.

7. The sensor of claim 6, wherein the emitter elements are LEDs of specific wavelengths, and the detector elements are silicon photodiode detectors that are complementary to the LEDs.

8. A method of measuring a blood parameter transcutaneously in the vascular system of a patient having a vascular access site, using a sensor comprising two pairs of complementary emitter and detector elements, wherein the pairs of emitter and detector elements define two lines at right angles to each other, the method comprising the steps of:
    placing the sensor at a measurement site on the skin of a patient with one of the pairs of emitter and detector elements parallel to the vascular access site and the other of the pairs of emitter and detector elements perpendicular to the vascular access site;

perturbing a region of the vascular system upstream of the measurement site;

using the sensor to transcutaneously measure the perturbation over a predetermined period of time at the measurement site; and calculating the blood parameter based on the measured perturbation.

9. The method of claim 8, wherein the perturbation is accomplished by injecting a marker into an upstream end of the vascular access site.

10. The method of claim 9, wherein the marker is a saline solution.

11. The method of claim 9, wherein the marker is tagged red blood cells.

12. The method of claim 8, wherein the perturbation is accomplished by changing a parameter of the blood.

13. A method of transcutaneously measuring access blood flow in a hemodialysis circuit including a vascular access site having an arterial needle site and a venous needle site downstream of the arterial needle site, a dialyzer having an inlet and an outlet, a dialysis arterial line connecting the dialyzer inlet to the arterial needle site, and a dialysis venous line connecting the dialyzer outlet to the venous needle site, using a sensor capable of determining the relative changes in hematocrit in the access blood flowing under the skin, the sensor comprising two pairs of complementary emitter and detector elements, wherein the pairs of emitter and detector elements define two lines at right angles to each other, the method comprising the steps of:

placing the sensor on the skin with one of the pairs of emitter and detector elements parallel to and over the vascular access site downstream of the venous needle site, and with the other of the pairs of emitter and detector elements perpendicular to the vascular access site;

using the sensor to output a signal proportional to the hematocrit in the vascular access site ($H_a$);

recording the signal with a monitoring system associated with the sensor;

obtaining a stable baseline $H_a$ value;

after a stable is $H_a$ obtained, injecting a known volume (V) of a reference diluent into the dialysis venous line upstream of the sensor; and using the signals produced from the time the diluent is injected to the time the signal returns to the baseline value to calculate access blood flow based on the ratio of percent change in hematocrit DH to a time-dependent hematocrit H using the monitoring system.

14. The method of claim 13, wherein access blood flow is calculated using a transient formulation.

15. The method of claim 13, wherein access blood flow is calculated using a steady state formulation.

16. A method of transcutaneously measuring access blood flow at an access site in a patient cardiovascular circuit using a sensor comprising two pairs of complementary emitter and detector elements, wherein the pairs of emitter and detector elements define two lines at right angles to each other, comprising the steps of:

placing the sensor on the skin of a patient with one of the pairs of emitter and detector elements parallel to and over the vascular access site and with the other of the pairs of emitter and detector elements perpendicular to the vascular access site;

infusing a specific volume ($V_i$) of an indicator diluent into the patient cardiovascular circuit at the access site in the presence of a hemodialysis circuit to effect a change in a blood parameter; and using the sensor to measure the percent change in the parameter.

17. The method of claim 16, wherein the blood parameter is selected from the group consisting of bulk density, flow energy, hematocrit, and red cell oxygen content.

* * * * *